United States Patent
Oh et al.

(10) Patent No.: US 9,650,325 B2
(45) Date of Patent: May 16, 2017

(54) COMPOUND, PREPARING METHOD THEREOF, AND USE THEREOF AS INHIBITORS OF HISTONE DEMETHYLASE

(71) Applicants: SNU R&DB FOUNDATION, Seoul (KR); KOREA INSTITUTE OF SCIENCE AND TECHNOLOGY, Seoul (KR); INDUSTRY-ACADEMIC COOPERATION FOUNDATION, YONSEI UNIVERSITY, Seoul (KR)

(72) Inventors: Dong-Chan Oh, Seoul (KR); Seong-Hwan Kim, Seoul (KR); Jongheon Shin, Daejeon (KR); Hak Cheol Kwon, Gangwon-do (KR); So Hee Kwon, Incheon (KR)

(73) Assignees: SNU R&DB FOUNDATION, Seoul (KR); INDUSTRY-ACADEMIC COOPERATION FOUNDATION, YONSEI UNIVERSITY, Seoul (KR); KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 37 days.

(21) Appl. No.: 14/243,488

(22) Filed: Apr. 2, 2014

(65) Prior Publication Data
US 2015/0133564 A1   May 14, 2015

(30) Foreign Application Priority Data
Nov. 13, 2013  (KR) .......................... 10-2013-0137884

(51) Int. Cl.
| | |
|---|---|
| *C12R 1/465* | (2006.01) |
| *A61K 31/122* | (2006.01) |
| *C07C 49/747* | (2006.01) |
| *C12P 7/26* | (2006.01) |

(52) U.S. Cl.
CPC .......... *C07C 49/747* (2013.01); *A61K 31/122* (2013.01); *C12P 7/26* (2013.01); *C12R 1/465* (2013.01); *C12Y 114/11* (2013.01); *C12Y 114/11027* (2013.01)

(58) Field of Classification Search
CPC ....... C07C 49/747; C12P 7/26; A61K 31/122; C12R 1/465; C12Y 114/11; C12Y 114/11027
See application file for complete search history.

(56) References Cited

U.S. PATENT DOCUMENTS 2,109,015 A *  2/1938  Niederl .................. C07C 37/16
                                                        568/308
2008/0255239 A1* 10/2008  Chow ................... C07C 275/24
                                                        514/596

FOREIGN PATENT DOCUMENTS

CN        103351275 A     10/2013
WO     WO 2008025361 A1 *  3/2008  ........... C07D 209/14

OTHER PUBLICATIONS

Hara et. al., Tetrahedron Letters, 1998, Pergamon, vol. 39, pp. 2589-2592.*
Nishimura et. al., Tetrahedron: Asymmetry, 2008, Elsevier, vol. 19, pp. 1778-1783.*
Davis et. al., Journal of the Chemical Society, Perkin Transactions I: Organic and Bio-Organic Chemistry, 1979, Royal Society of Chemistry, vol. 12, pp. 3001-3003.*
Sheridan et al., "Synthesis and pharmacological activity of aminoindanone dimers and related compounds", Bioorganic & Medicinal Chemistry, vol. 16, pp. 248-254, (2008).
Mazzocchi et al., "Synthesis and Pharmacological Properties of 1,2,3,4,5,6-Hexahydro-1,6-methano-2-benzazocines", J. Med. Chem., vol. 24, pp. 457-462, (1981).
Arp et al., "Catalytic Enantioselective Negishi Reactions of Racemic Secondary Benzylic Halides", J. Am. Chem. Soc., vol. 127, pp. 10482-10483, (2005).
Bloom et al., "Metal-Catalyzed Benzylic Fluorination as a Synthetic Equivalent to 1,4-Conjugate Addition of Fluoride", J. Org. Chem., vol. 78, pp. 11082-11086, (2013).
Korean Official Action mailed May 21, 2015, eight pages.
Kim, et al., Tripartin, a Histone Demethylase Inhibitor from a Bacterium Associated with a Dung Beetle Larva, Org. Lett., vol. XX, No. XX, pp. XXXX, disclosed on Apr. 19, 2013.

* cited by examiner

*Primary Examiner* — Sarah Pihonak
(74) *Attorney, Agent, or Firm* — Vorys, Sater, Seymour & Pease LLP; Mih Suhn Koh

(57) ABSTRACT

Provided are a novel compound, preparing method thereof, and use thereof as inhibitor of histone demethylase. The compound represented by Chemical Formula 1 has activity which inhibits histone demethylase and thus is capable of specifically and effectively inhibit activity of histone demethylase.

14 Claims, 2 Drawing Sheets

SEQUENCE LISTING

```
<160> NUMBER OF SEQ ID NOS: 1

<210> SEQ ID NO 1
<211> LENGTH: 879
<212> TYPE: DNA
<213> ORGANISM: Artificial Sequence
<220> FEATURE:
<223> OTHER INFORMATION: 16S rDNA of Streptomyces sp. SNC023 strain

<400> SEQUENCE: 1
cacggcccag actcctacgg gaggcagcag tggggaatat tgcacaatgg gcgcaagcct      60
gatgcagcga cgccgcgtga gggatgacgg ccttcgggtt gtaaacctct ttcagcaggg     120
aagaagcgag agtgacggta cctgcagaag aagcgccggc taactacgtg ccagcagccg     180
cggtaatacg tagggcgcaa gcgttgtccg gaattattgg gcgtaaagag ctcgtaggcg     240
gcttgtcgcg tcggttgtga aagcccgggg cttaaccccg ggtctgcagt cgatacgggc     300
aggctagagt tcggtagggg agatcggaat tcctggtgta gcggtgaaat gcgcagatat     360
caggaggaac accggtggcg aaggcggatc tctgggccga tactgacgct gaggagcgaa     420
agcgtgggga gcgaacagga ttagataccc tggtagtcca cgccgtaaac ggtgggcact     480
aggtgtgggc aacattccac gttgtccgtg ccgcagctaa cgcattaagt gccccgcctg     540
gggagtacgg ccgcaaggct aaaactcaaa ggaattgacg ggggcccgca caagcggcgg     600
agcatgtggc ttaattcgac gcaacgcgaa gaaccttacc aaggcttgac atacaccgga     660
aagcatcaga gatggtgccc cccttgtggt cggtgtacag gtggtgcatg gctgtcgtca     720
gctcgtgtcg tgagatgttg ggttaagtcc cgcaacgagc gcaacccttg tcccgtgttc     780
cagcaactct tcggaggttg gggactcacg ggagaccgcc ggggtcaact cggaggaagg     840
tggggacgac gtcaatcatc atgcccctta tgttcttgg                            879
```

COMPOUND, PREPARING METHOD THEREOF, AND USE THEREOF AS INHIBITORS OF HISTONE DEMETHYLASE

RELATED APPLICATIONS

This application claims the benefit of Korean Patent Application No. 10-2013-0137884, filed on Nov. 13, 2013, in the Korean Intellectual Property Office, the disclosure of which is incorporated herein in its entirety by reference.

The Sequence Listing submitted in text format (.txt) filed on Apr. 2, 2014, named "SequenceListing.txt", created on Apr. 2, 2014, 1.50 KB), is incorporated herein by reference.

BACKGROUND

1. Field

One or more embodiments of the present invention relate to a novel compound, a preparing method thereof, and a use thereof as an inhibitor of histone demethylase.

2. Description of the Related Art

Transcriptional regulation in a cell is a complicated biological procedure. One of the transcriptional regulation mechanisms is post-transcriptional modification of eight histone proteins forming a histone core complex, which are also called histone proteins H2A/B, H3, and H4. N-terminal modification of histone proteins may be, for example, acetylation or methylation of a lysine residue or phosphorylation of a serine residue. Such a medication may change affinity between a histone and a DNA and thereby regulate gene expression.

Methylation of a histone may inhibit or activate transcription. A methyl group is added to a histone by histone lysine methyltransferase (HMT or KMT), while a methyl group bound to a histone is removed by histone lysine demethylase (KDM). KMT is specific to lysine or arginine and may combine one to three methyl groups with a target amino acid residue. KDM is classified as KDM1, KDM2, KDM3, KDM4, KDM5, KDM6, and KDM7 based on the substrate specificity and protein domain structure thereof. An inhibitor of KTM is, for example, chaetocin, DANep, BIX-01294, EGCG, sinefungin, adenoine dialdehyde, and novobiocin. An inhibitor of KDM is, for example, tranylcyprome, phenelzine, a polyamine analogue, N-oxalyglycine (NOG), disulfuram, ebselen, and an N-oxalyl D-tyrosine derivative. These inhibitors are very rare. Therefore, it is necessary to search for an inhibitor which may specifically inhibit KTM or KDM.

A biological approach has come to the fore in natural product research to search for a structurally novel bioactive substance. In recent, studies of bacteria, which are originated from biological backgrounds of insect, have been made actively. In addition, there is need to screen biologically active molecules from bacteria discovered in an environment in which insects grow.

While screening and studying insect-derived microbes, a novel strain producing a novel compound was discovered and KDM activity of the compound was verified to complete the present invention.

SUMMARY

One or more embodiments of the present invention provide a novel compound, an isomer thereof, a derivative thereof, and a pharmaceutically allowable salt thereof.

One or more embodiments of the present invention provide a strain producing the compound.

One or more embodiments of the present invention provide a method of producing the compound.

One or more embodiments of the present invention provide an inhibitor of histone lysine demethylase, which is the compound.

One or more embodiments of the present invention provide a method of inhibiting activity of histone lysine demethylase in a subject.

In addition, one or more embodiments of the present invention provide a method of inhibiting activity of histone lysine demethylase including in vitro incubation using the compound.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
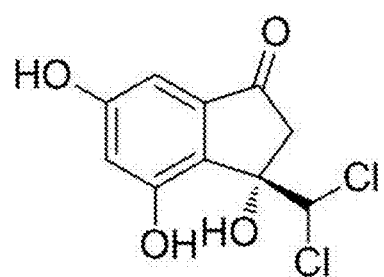
FIG. 1 is a chemical formula of tripartin.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description.

An aspect of the present invention provides a compound represented by Chemical Formula 1, an isomer thereof, a derivative thereof, and a pharmaceutically allowable salt thereof.

An aspect of the present invention provides a *Streptomyces* genus SNC023 strain producing the compound.

An aspect of the present invention provides a method of preparing the compound.

An aspect of the present invention provides an inhibitor of histone lysine demethylase, which is the compound.

An aspect of the present invention provides a method of inhibiting activity of histone lysine demethylase in a subject.

In addition, an aspect of the present invention provides a method of inhibiting activity of histone lysine demethylase including in vitro incubation using the compound.

An aspect of the present invention provides a compound represented by Chemical Formula 1 below, an isomer thereof, a derivative thereof, and a pharmaceutically allowable salt thereof.

[Chemical Formula 1]

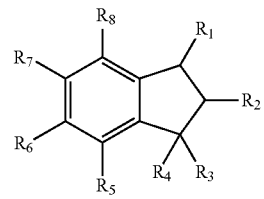

The term "isomers" used herein refers to compounds having an identical molecular formula but a different atomic connection or space arrangement with each other. An isomer may include, for example, a structural isomer and a stereoisomer.

The term "derivative" used herein refers to a compound obtained by substituting another atom or atomic group for a part of the structure of the compound.

The term "pharmaceutically allowable salt" refers to an inorganic or organic additive salt of a compound.

In Chemical Formula 1, $R_1$ may be hydrogen, a hydroxyl group, a ketone group, a halogen group, a substituted or unsubstituted $C_1$ to $C_{20}$ alkly group, a cyano group, or a combination thereof. When $R_1$ is a ketone group, the compound may be an indanone compound.

In Chemical Formula 1, $R_2$, $R_3$, $R_4$, $R_5$, $R_6$, $R_7$, and $R_8$ may independently be hydrogen, a hydroxyl group, a halogen group, a cyano group, —C(=O)$R_a$, —C(=O)O$R_a$, —OCO(O$R_a$), —C=N($R_a$), —S$R_a$, —S(=O)$R_a$, —S(=O)$_2R_a$, —P$R_a$, a substituted or unsubstituted $C_1$ to $C_{20}$ alkly group, a substituted or unsubstituted $C_2$ to $C_{20}$ alkoxy group, a substituted or unsubstituted $C_2$ to $C_{20}$ alkenyl group, a substituted or unsubstituted $C_2$ to $C_{20}$ alkynyl group, a $C_2$ to $C_{20}$ alkylene oxide group, a substituted or unsubstituted $C_3$ to $C_{30}$ cycloalkyl group, a substituted or unsubstituted $C_6$ to $C_{30}$ aryl group, a substituted or unsubstituted $C_6$ to $C_{30}$ aryloxy group, a substituted or unsubstituted $C_6$ to $C_{30}$ heteroaryl group, or a combination thereof, and $R_a$ may be hydrogen, a $C_1$ to $C_{10}$ alkly group, or a $C_6$ to $C_{20}$ aryl group. The term "substitution" in the term "substituted" refers to introducing a different atomic group instead of a hydrogen atom, when a derivative is formed by substituting a different atomic group for a hydrogen atom, and the term "substituted group" refers to an introduced atomic group. A substituted group may be a halogen atom, a $C_1$ to $C_{20}$ alkly group (e.g., $CCF_3$, $CHCF_2$, $CH_2F$, $CCl_3$, etc.), a hydroxyl group, a nitro group, a cyano group, an amino group, an amidino group, hydrazine, hydrazone, a carboxyl group or a salt thereof, a sulfonate group or a salt thereof, a phosphate or a salt thereof, a $C_1$ to $C_{20}$ alkyl group, a $C_2$ to $C_{20}$ alkenyl group, $C_2$ to $C_{20}$ alkynyl group, a $C_1$ to $C_{20}$ heteroalkyl group, a $C_6$ to $C_{20}$ aryl group, a $C_6$ to $C_{20}$ arylalkyl group, a $C_6$ to $C_{20}$ heteroaryl group, or a $C_6$ to $C_{20}$ heteroarylakyl group. The $C_1$ to $C_{20}$ alkly group may be, for example, $C_1$ to $C_{15}$, $C_1$ to $C_{10}$, $C_1$ to $C_5$, or $C_1$ to $C_3$ alkyl group. The alkyl group may be, for example, a methyl group. The $C_2$ to $C_{20}$ alkenyl group may be, for example, a $C_2$ to $C_{15}$, $C_2$ to $C_{10}$, or $C_2$ to $C_5$ alkenyl group. The $C_2$ to $C_{20}$ alkynyl group may be, for example, a $C_2$ to $C_{15}$, $C_2$ to $C_{10}$, or $C_2$ to $C_5$ alkynyl group. The $C_6$ to $C_{30}$ aryl group may be, for example, a $C_6$ to $C_{15}$, or $C_6$ to $C_{10}$ aryl group.

In Chemical Formula 1, $R_2$, $R_3$, $R_4$, $R_5$, $R_6$, and $R_7$ may independently be hydrogen, a hydroxyl group, or a substituted or unsubstituted $C_1$ to $C_{20}$ alkly group. The $C_1$ to $C_{20}$ alkly group is described above. For example, the $R_3$, $R_4$, and $R_6$ may independently be a hydroxyl group.

In Chemical Formula 1, $R_3$ may be a halogen atom, or a $C_1$ to $C_{20}$ alkly group substituted with a halogen atom. A halogen atom refers to an atom belonging to Family 17 of the periodic table. A halogen atom may be, for example, fluorine, chlorine, bromide, or iodine. The $C_1$ to $C_{20}$ alkly group is described above. The $R_3$ may be a $C_1$ to $C_5$ alkly group substituted with a halogen atom. For example, $R_3$ may be a $C_1$ to $C_5$ alkly group substituted with two halogen atoms.

The compound may be a compound represented by Chemical Formula 2.

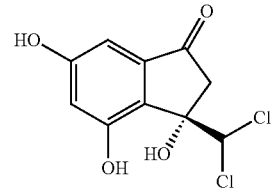

[Chemical Formula 2]

An aspect of the present invention provides a *Streptomyces* genus SNC023 strain producing the compound, wherein the *Streptomyces* genus SNC023 strain has been deposited under Korean Collection for Type Cultures (KCTC) Accession number KCTC12494BP.

The strain may produce the compound represented by Chemical Formula 1. The compound represented by Chemical Formula 1 is described above.

The strain includes a mutant thereof. A mutant may be, for example, a mutant produced by natural mutation or artificial mutation. Artificial mutation may be caused by a physical mutagen or a chemical mutagen such as a basic compound.

The strain includes a spore, microbial cell, or a culturing product thereof.

The strain may be separated or derived from the epidermis or body of a larva included in a brood ball of *Copris tripartitus*.

An aspect of the present invention provides a method of producing a novel compound, wherein the method includes culturing a *Streptomyces* genus SNC023 strain (Accession NO: KCTC12494BP) and separating the compound represented by Chemical Formula 1 from the culturing medium.

The method includes culturing a *Streptomyces* genus SNC023 strain, wherein the *Streptomyces* genus SNC023 strain has been deposited under KCTC Accession number KCTC12494BP.

The culturing may be culturing the strain in a liquid medium or a solid medium. A medium may include as a carbon source, for example, glucose, starch syrup, dextrin, starch, molasses, animal oils, or vegetable oils. A medium may include as a nitrogen source, for example, wheat bran, soybean meal, wheat, malt, cotton seed meal, fish scraps, corn steep liquor, meat extract, a yeast extract, ammonium sulfate, natrium nitrate, and urea. When necessary, the medium may include a culinary salt, potassium, magnesium, cobalt, chlorine, phosphoric acid, sulfuric acid, and other inorganic salts enhancing other ion generation.

The culturing may be culturing under aerobic conditions with agitation or in a stationary manner. The culturing temperature may be, for example, from about 20° C. to about 37° C. or from about 26° C. to about 30° C.

The culturing includes separating the compound represented by Chemical Formula 1 above from the culturing medium.

The separating of the compound represented by Chemical Formula 1 above from the culturing medium may include performing concentration, centrifugation, filtration, or chromatography on the culturing medium. The chromatography may be, for example, column chromatography, planar chromatography, paper chromatography, or thin-layer chromatography, according to a stationary phase type. The chromatography may be, for example, gas chromatography, liquid chromatography, or affinity chromatography, according to the physical properties of a mobile phase. Liquid chromatography may be, for example, high performance liquid chromatography (HPLC). The chromatography may be, for example, ion exchange chromatography or size exclusion chromatography, according to the separation method. The chromatography may be, for example, normal phase chromatography or reverse-phase chromatography.

An aspect of the present invention provides a compound represented by Chemical Formula 1, an isomer thereof, a derivative thereof, and a pharmaceutically allowable salt thereof, which is an inhibitor of histone lysine demethylase (KDM).

The compound represented by Chemical Formula 1, an isomer thereof, a derivative thereof, and a pharmaceutically allowable salt thereof are described above.

The compound represented by Chemical Formula 1 may be an inhibitor which inhibits activity of KDM. The term "demethylase" refers to an enzyme removing a methyl group from a nucleic acid, a protein, or another molecule.

KDM may remove a methyl group from an amino acid of a histone protein. A substrate of KDM is specified according to histone subunit (H1, H2A, H2B, H3, and H4), sequence of amino acids, and number of methyl groups. A substrate having 1, 2 or 3 methyl group may be referred to as "me1," "me2," and "me3," respectively. For example, "H3K9me3" refers to histone H3 with a tri-methylated lysine in the ninth position. A KDM may be KDM1, KDM2, KDM3, KDM4, KDM5, or KDM6. KDM1 employs H3K4me2/1 and H3K9me2/1 as a substrate and includes KDM1A (also called LSD1, BHC110, or AOF2) and KDM1B (also called LSD2 or AOF1). KDM2 employs H3K36me2/1 as a substrate and includes KDM2A (also called JHDM1A or FBXL11) and KDM2B (also called JHDM1B or FBXL10). KDM3 employs H3K9me2/1 as a substrate and includes KDM3A (also called JMJD1A, JHDM2A, or TSGA), KDM3B (also called JMJD1B, JHDM2B, or 5qNCA), and KDM3C (also called JMJD1C, JHDM2C, or TRIP8). KDM4 employs H3K9me3/2 and H3K36me3/2 as a substrate and includes KDM4A (also called JMJD2A or JHDM3A), KDM4B (also called JMJD2B or JHDM3B), KDM4C (also called JMJD2C, JHDM3C, or GASC1), and KDM4D (also called JMJD2D or JHDM3D). KDM5 H3K4me3/2 as a substrate and includes KDM5A (also called JARID1A or RBP2), KDM5B (also called JARID1B or PLU-1), KDM5C (also called JARID1C or SMCX), and KDM5D (also called JARID1D or SMCY). KDM6 employs H3K27me3/2 as a substrate and includes KDM6A (also called UTX) and KDM6B (also called JMJD3). A human KDM subfamily may be KDM2/7, KDM3, KDM4, KDM5, or KDM6. For example, KDM2/7, KDM3, KDM4, KDM5, and KDM6 may demethylate H3K36, H3K9me2/1, H3K9me3, H3K4, and H3K27, respectively. For example, the compound represented by Chemical Formula 1, an isomer thereof, a derivative thereof, and a pharmaceutically allowable salt thereof may have activity to inhibit KDM4. The KDM4 may demethylate histone H3 with a tri-methylated lysine in the ninth position.

An aspect of the present invention provides a method of inhibiting activity of KDM in a subject, wherein the method includes contacting the compound represented by Chemical Formula 1, an isomer thereof, a derivative thereof, or a pharmaceutically allowable salt thereof with KDM.

The compound represented by Chemical Formula 1, an isomer thereof, a derivative thereof, and a pharmaceutically allowable salt thereof are described above.

The contacting may be performed in vivo. The contacting may be administrating the compound represented by Chemical Formula 1, an isomer thereof, a derivative thereof, and a pharmaceutically allowable salt thereof into a body of a subject.

The administrating method may be oral administration, rectum administration, intramuscular, subcutaneous, intrauterine epidural, or intracerebroventricular injection. An appropriate dose of the compound is dependent on patient state, weight, severity of disease, type of drug, and administration pathway and period, but may be properly chosen by those of ordinary skill in the art. However, the compound represented by Chemical Formula 1 may be administrated by an amount of about 0.0001 mg/kg to about 100 mg/kg, or about 0.001 mg/kg to about 100 mg/kg by dividing the amount into more than one dose.

The subject may be a mammal such as a rat, a mouse, a domestic animal, or a human.

The compound represented by Chemical Formula 1, an isomer thereof, a derivative thereof, or a pharmaceutically allowable salt thereof may be contacted with KDM to inhibit KDM activity in a subject. KDM activity may be inhibited to increase antibacterial or antifungal activity, prevent or treat a cancer or Alzheimer's disease, or prevent or treat an infectious disease induced or caused by a microorganism. The cancer may be prostate cancer, esophageal cancer, lung cancer, lymphoma, colorectal cancer, or breast cancer. The term "prevention" used herein refers to any action resulting in the suppression or delay of the onset of a disease owing to the administration of the composition according to the present invention. The term "treatment" used herein refers to any action resulting in improvements in symptoms a disease or the beneficial alteration of the disease state owing to the administration of the composition according to the present invention.

An aspect of the present invention provides a method of inhibiting activity of KDM including incubating in vitro the compound represented by Chemical Formula 1, an isomer thereof, a derivative thereof, or a pharmaceutically allowable salt thereof with KDM.

The compound represented by Chemical Formula 1, an isomer thereof, a derivative thereof, and a pharmaceutically allowable salt thereof are described above.

The incubating may be performed at a temperature from about 0 to about 40° C. The incubating may be performing mixing, vortexing, or stirring. The incubating may be performed from about 30 seconds to about 24 hours.

Hereinafter, the present invention will be described in further detail with reference to examples. It will be obvious that these examples are illustrative purposes only and are not to be construed to limit the scope of the present invention.

Example 1

Separation of *Streptomyces* Genus SNC023 Strain

To screen a strain producing a substance having novel biological activity, SNC023 strain was separated from the epidermis and body of a larva included in a brood ball of *Copris tripartitus* provided by the Rural Development Administration of Korea. A whole genome of the SNC023 strain was separated to perform cloning and then sequencing of the 16S ribosomal DNA in the whole genome (SEQ ID NO: 1).

As a result of the sequencing, the SNC023 strain was identified as a *Streptomyces* sp. genus strain. The strain was named *Streptomyces* genus SNC023 strain and deposited under Korean Collection for Type Cultures (KCTC), Korea Research Institute of Bioscience and Biotechnology (KRIBB), 125 Gwahak-ro, Yuseong-gu, Daejeon 305-806, Republic of Korea, on Sep. 26, 2013 (Accession number KCTC12494BP). Access to the deposits will be available during the pendency of the application to the Commissioner of Patents and Trademarks and persons determined by the Commissioner to be entitled thereto upon request. The deposits will be maintained in the KCTC Depository, which is a public depository, for a period of 30 years, or 5 years after the most recent request, or for the enforceable life of the patent, whichever is longer, and will be replaced if it becomes nonviable during that period. Applicant does not waive any infringement of their rights granted under this patent.

Example 2

Culturing of *Streptomyces* Genus SNC023 Strain

Figure 2:
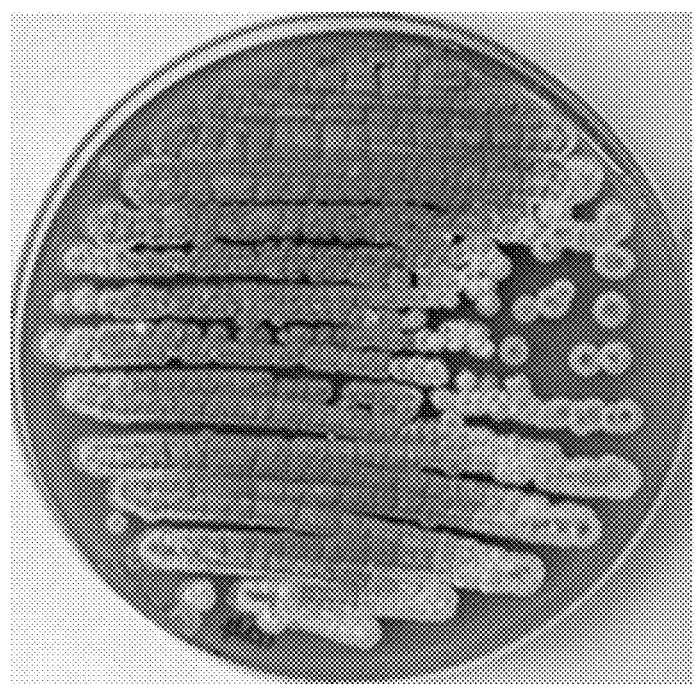
FIG. 2 is an image of a *Streptomyces* genus SNC023 strain cultured in a solid plate medium.

The *Streptomyces* genus SNC023 strain was inoculated to a sterilized solid medium (10 g of malt extract, 4 g of yeast extract, 2 g of glucose, and 18 g of agar per 1 L of water) and the primary culturing was performed at 30° C. for a few days. FIG. 2 shows an image of the SNC023 strain cultured in the solid medium.

The SNC023 strain cultured in the solid medium was inoculated to 50 ml of fertilized YPM liquid medium (10 g of mannitol, 4 g of yeast extract, 2 g of peptone per 1 L of water), and the resulting culturing medium was agitated at 200 rpm at 30° C. for two days to perform the secondary culturing. 10 ml of the secondary culturing medium was inoculated to 1 L of YPM liquid medium, and the resulting culturing medium was agitated at 200 rpm at 30° C. for eight days to perform the tertiary culturing.

Example 3

Separation and Purification of Tripartin

1 L of ethyl acetate was added to 1 L of the SNC023 strain culturing medium of Example 2 and mixed for 30 seconds. The mixture was then kept for three minutes so that an ethyl acetate layer and an aqueous layer might be separated. After removing the aqueous layer, the ethyl acetate layer was filtered with a filter paper. 100 g of anhydrous sodium sulfate was added to the filtered liquid to remove the remaining water. From the filtered liquid from which water had been removed, a crude extract was obtained by using a concentrator. The remaining water layer was once again extracted by using 1 L of ethyl acetate. This procedure was repeated for 40 times to obtain 10 g of extract. The obtained extract was divided into six fractions by performing reverse-phase chromatography (Sepak® $C_{18}$ 2 g, reversed-phase). An eluent for the six fractions was prepared by reducing 20% water each time from 80% (v/v) water/methanol. The last fraction was obtained by 50% (v/v) methanol/dichloromethane. A total of six fractions (20 ml each) were obtained.

The Fraction 2 obtained by using 60% (v/v) water/methanol was analyzed by liquid chromatography-mass spectroscopy (LC/MS) and hydrogen nuclear magnetic resonance (NMR) spectroscopy, and the result showed that the culturing medium of the strain included tripartin. The LC/MS analysis was performed by using an LC/MS instrument formed by connecting Agilent Technologies 1200 Series LC and 6130 MS. The Fraction 2 concentrated by vacuum drying was dissolved in 20 ml of methanol, and the resulting solution was separated by using $C_{18}$ reversed-phase semi-preparative HPLC column (particle diameter 5 mm, 250×10 mm (length×inner diameter), eluting rate 2 ml/min, UV detector) (Kromasil) in a gradient system (70% (v/v)→35% (v/v) water/methanol, 50 minutes). After the separation, 7.0 mg of tripartin was obtained.

Example 4

Analysis of Physicochemical Properties of Tripartin

Tripartin was a white-colored solid which was stable at room temperature and well dissolved in an intermediate organic solvent such as methanol and acetone. The structure of tripartin was determined by using nuclear magnetic resonance spectrum data, infrared-UV spectroscopy data, and high-resolution mass spectroscopy data. NMR ($^1$H NMR, $^{13}$C NMR) was performed by using a 500 MHz NMR instrument (Bruker) and DMSO-$d_6$ solvent. Mass spectroscopy was performed by using JMS-700 GC-MS CI MS (Jeol) and the data were presented in mass/charge (m/z). An infrared spectrum was obtained by using a FT-IR-4200 spectrometer (Jasco). A UV spectrum was obtained by using a U-3010 UV/VIS spectrometer (Hitachi).

Table 1 shows the structural site direction of traipartin by NMR spectrum.

[Tripartin]
(1) Molecular formula: $C_{10}H_8Cl_2O_4$
(2) Molecular weight: 263
(3) Color: white
(4) Infrared absorption (neat): 3360, 3195, 2924, 2853, 1659 $cm^{-1}$
(5) $^1$H-NMR (DMSO-$d_6$, 500 MHz): Refer to Table 1
(6) $^{13}$C-NMR (DMSO-$d_6$, 125 MHz): Refer to Table 1

TABLE 1

NMR Data of Tripartin

| C/H | $\delta_H{}^a$ | mult (J in Hz) | $\delta_C{}^b$ | | HMBC |
|---|---|---|---|---|---|
| 1 | | | 201.8 | C | |
| 2a | 3.10 | d (18.9) | 47.2 | $CH_2$ | 1, 3, 8, 9, 10 |
| 2b | 2.62 | d (18.9) | | | 1, 3, 8, 9, 10 |
| 3 | | | 80.2 | C | |
| 4 | | | 155.7 | C | |
| 5 | 6.57 | d (1.8) | 109.2 | CH | 3, 4, 6, 7, 9 |
| 6 | | | 160.4 | C | |
| 7 | 6.41 | d (1.8) | 98.5 | CH | 1, 5, 6, 9 |
| 8 | | | 139.2 | C | |
| 9 | | | 131.1 | C | |
| 10 | 6.66 | s | 76.7 | CH | 2, 3, 9 |

$^a$500 MHZ,
$^b$125 MHz)

Example 5

Verification of Histone Demethylase (KDM) Inhibitory Activity of Tripartin

HeLa cell line, which is a uterine cervical cancer cell line, was treated with tripartin and then histone was extracted from the tripartin-treated HeLa cell. A histone methylation antibody which may verify activity of the KDM was analyzed by immunoblotting to measure the KDM inhibiting effect.

Figure 3:
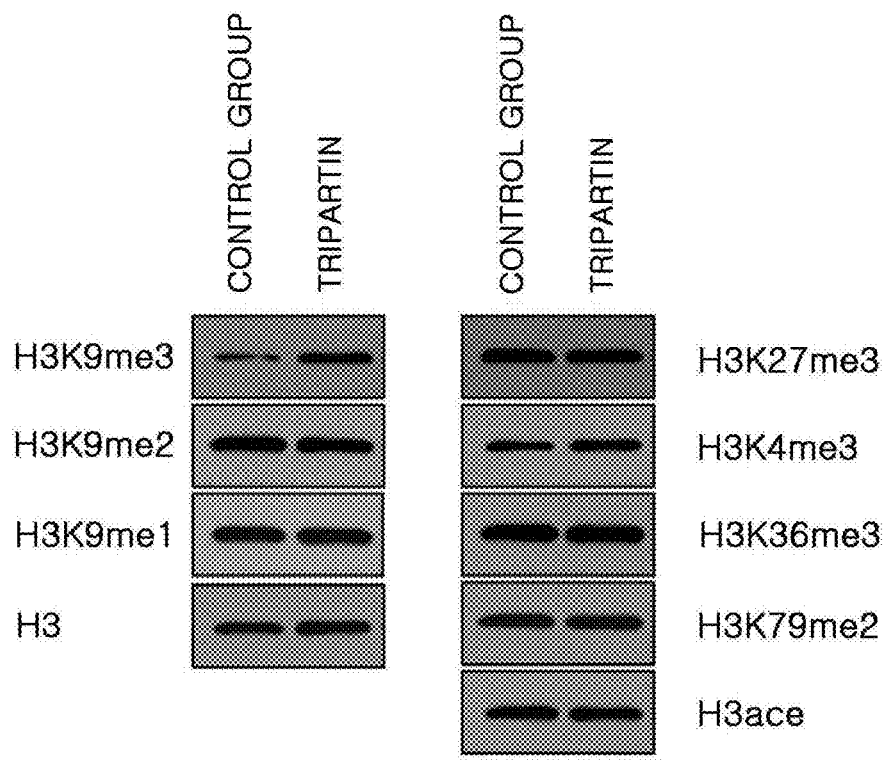
FIG. 3 is an immunoblotting image of a histone separated from tripartin-treated HeLa cell line.

0.1% (w/v) DMSO (control group), or 0.1% (w/v) DMSO and 10 μM tripartin (experimental group) was added to the HeLa cell line, which was then incubated at 37° C. for 24 hours. Subsequently, proteins were extracted from the HeLa cell line, and the extracted proteins underwent electrophoresis with 15% SDS-polyacrylamide. Anti-histone H3 antibody (MILLIPORE), anti-H3K9me3 antibody (MILLI- PORE), anti-H3K9me2 antibody (MILLIPORE), anti-H3K3me1 antibody (MILLIPORE), anti-H3K27me3 antibody (MILLIPORE), anti-H3K4me3 antibody (MILLIPORE), anti-H3K36me3 antibody (MILLIPORE), anti-H3K79me2 antibody (MILLIPORE), and anti-H3ace antibody (MILLIPORE) were used to perform immunoblotting. FIG. 3 shows the results. Herein, "H", "K", "me", and "ace" refer to histone, lysine (K), methylation, and acetylation, respectively. The number next to "H" refers to a histone number, the number next to "K" refers to the histone amino acid number, and the number next to "me" refers to the number of methylation. For example, "H3K9me3" refers to histone H3 with a tri-methylated lysine in the ninth position.

As shown in FIG. 3, H3K9me1, H3K9me2, H3, H3K27me3, H3K4me3, H3K36me3, H3K79me2, and H3ace were not increased, while H3K9me3 was increased significantly. KDM3, KDM4, KDM6, KDM5, and KDM2/7 demethylate H3K9me2/1, H3K9me3, H3K27, H3K4, and H3K36, respectively. No inhibitory effect was found in the KDM2/7, KDM3, KDM5, and KDM6 groups. However, it was verified that tripartin (10 μM) have an inhibitory effect with respect to KDM4 in comparison to the DMSO control group.

[Accession Number]

Identification of the microorganism: *Streptomyces diastaticus* SNC023

Accession number: KCTC12494BP

Date of Deposit: Sep. 26, 2013

Name and Address of Depository:

Korean Collection for Type Cultures (KCTC),

Korea Research Institute of Bioscience and Biotechnology (KRIBB),

125 Gwahak-ro, Yuseong-gu, Daejeon 305-806, Republic of Korea

As described above, according to the one or more of the above embodiments of the present invention, the compound represented by Chemical Formula 1 has activity which inhibits KDM and thus is capable of specifically and effectively inhibit activity of KDM.

It should be understood that the exemplary embodiments described therein should be considered in a descriptive sense only and not for purposes of limitation. Descriptions of features or aspects within each embodiment should typically be considered as available for other similar features or aspects in other embodiments.

While one or more embodiments of the present invention have been described with reference to the figures, it will be understood by those of ordinary skill in the art that various changes in form and details may be made therein without departing from the spirit and scope of the present invention as defined by the following claims.

What is claimed is:

1. A compound represented by Chemical Formula 1, an isomer thereof, or a pharmaceutically acceptable salt thereof:

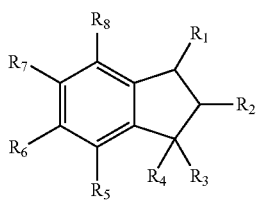

[Chemical Formula 1]

wherein,
$R_1$ is a ketone group, a halogen group, a substituted or unsubstituted $C_1$ to $C_{20}$ alkyl group, a cyano group, or a combination thereof;
$R_2$ is hydrogen, a halogen group, a cyano group, —C(=O)$R_a$, —C(=O)O$R_a$, —OCO(O$R_a$), —C=N($R_a$), —S$R_a$, —S(=O)$R_a$, —S(=O)$_2R_a$, —P$R_a$, a substituted or unsubstituted $C_1$ to $C_{20}$ alkyl group, a substituted or unsubstituted $C_2$ to $C_{20}$ alkoxy group, a substituted or unsubstituted $C_2$ to $C_{20}$ alkenyl group, a substituted or unsubstituted $C_2$ to $C_{20}$ alkynyl group, a $C_2$ to $C_{20}$ alkylene oxide group, a substituted or unsubstituted $C_3$ to $C_{30}$ cycloalkyl group, a substituted or unsubstituted $C_6$ to $C_{30}$ aryl group, a substituted or unsubstituted $C_6$ to $C_{30}$ aryloxy group, a substituted or unsubstituted $C_6$ to $C_{30}$ heteroaryl group, or a combination thereof, and $R_a$ is hydrogen, a $C_1$ to $C_{10}$ alkyl group, or a $C_6$ to $C_{20}$ aryl group;
$R_4$ is a hydroxyl group, a halogen group, a cyano group, —C(=O)$R_a$, —C(=O)O$R_a$, —OCO(O$R_a$), —C=N($R_a$), —S$R_a$, —S(=O)$R_a$, —S(=O)$_2R_a$, —P$R_a$, a substituted or unsubstituted $C_1$ to $C_{20}$ alkyl group, a substituted or unsubstituted $C_2$ to $C_{20}$ alkoxy group, a substituted or unsubstituted $C_2$ to $C_{20}$ alkenyl group, a substituted or unsubstituted $C_2$ to $C_{20}$ alkynyl group, a $C_2$ to $C_{20}$ alkylene oxide group, a substituted or unsubstituted $C_3$ to $C_{30}$ cycloalkyl group, a substituted or unsubstituted $C_6$ to $C_{30}$ aryl group, a substituted or unsubstituted $C_6$ to $C_{30}$ aryloxy group, a substituted or unsubstituted $C_6$ to $C_{30}$ heteroaryl group, or a combination thereof, and $R_a$ is hydrogen, a $C_1$ to $C_{10}$ alkyl group, or a $C_6$ to $C_{20}$ aryl group; and
$R_5$, $R_6$, $R_7$, and $R_8$ are each independently hydrogen, a hydroxyl group, a halogen group, a cyano group, —C(=O)$R_a$, —C(=O)O$R_a$, —OCO(O$R_a$), —C=N($R_a$), —S$R_a$, —S(=O)$R_a$, —S(=O)$_2R_a$, —P$R_a$, a substituted or unsubstituted $C_1$ to $C_{20}$ alkyl group, a substituted or unsubstituted $C_2$ to $C_{20}$ alkoxy group, a substituted or unsubstituted $C_2$ to $C_{20}$ alkenyl group, a substituted or unsubstituted $C_2$ to $C_{20}$ alkynyl group, a $C_2$ to $C_{20}$ alkylene oxide group, a substituted or unsubstituted $C_3$ to $C_{30}$ cycloalkyl group, a substituted or unsubstituted $C_6$ to $C_{30}$ aryl group, a substituted or unsubstituted $C_6$ to $C_{30}$ aryloxy group, a substituted or unsubstituted $C_6$ to $C_{30}$ heteroaryl group, or a combination thereof, where $R_a$ is hydrogen, a $C_1$ to $C_{10}$ alkyl group, or a $C_6$ to $C_{20}$ aryl group; and
$R_3$ is a halogen group, a $C_1$ to $C_{20}$ alkyl group substituted with one or more halogen atoms, or a combination thereof; and wherein at least one of $R^5$, $R^6$, $R^7$, and $R^8$ is a hydroxyl group.

2. The compound, the isomer, or the pharmaceutically acceptable salt thereof of claim 1, wherein the $R_2$ is hydrogen, or a substituted or unsubstituted $C_1$ to $C_{20}$ alkyl group, $R_4$ is a hydroxyl group, or a substituted or unsubstituted $C_1$ to $C_{20}$ alkyl group, and $R_5$, $R_6$, $R_7$, and $R_8$ are independently hydrogen, a hydroxyl group, or a substituted or unsubstituted $C_1$ to $C_{20}$ alkyl group.

3. The compound, the isomer, or the pharmaceutically acceptable salt of claim 1, wherein $R_4$ and $R_6$ are each independently a hydroxyl group.

4. The compound, the isomer, or the pharmaceutically acceptable salt of claim 1, wherein $R_3$ is a $C_1$ to $C_5$ alkyl group substituted with two halogen atoms.

5. The compound, the isomer, or the pharmaceutically acceptable salt of claim 1, wherein the compound is further represented by Chemical Formula 2:

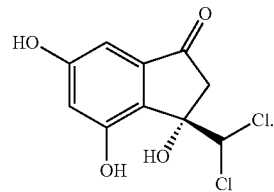

[Chemical Formula 2]

6. A method of producing the compound of claim 5, the method comprising:
culturing a *Streptomyces* genus SNC023 strain in a culturing medium, wherein the *Streptomyces* genus SNC023 strain is deposited under KCTC Accession number KCTC12494BP; and
separating the compound of claim 5 from the culturing medium.

7. The method of claim 6, wherein the separating the compound of claim 5 from the culturing medium comprises extracting the culturing medium by using ethyl acetate, water, or a combination thereof.

8. The method of claim 6, wherein the separating the compound of claim 5 from the culturing medium comprises performing concentration, centrifugation, filtration, or chromatography on the culturing medium.

9. An inhibitor of histone lysine demethylase (KDM), which is a compound represented by Chemical Formula 1, an isomer thereof, or a pharmaceutically acceptable salt thereof:

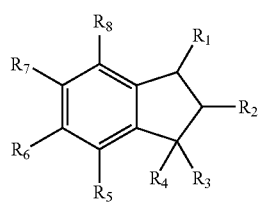

[Chemical Formula 1]

wherein,
$R_1$ is a ketone group, a halogen group, a substituted or unsubstituted $C_1$ to $C_{20}$ alkyl group, a cyano group, or a combination thereof;
$R_2$ is hydrogen, a halogen group, a cyano group, —C(=O)$R_a$, —C(=O)O$R_a$, —OCO(O$R_a$), —C=N($R_a$), —S$R_a$, —S(=O)$R_a$, —S(=O)$_2R_a$, —P$R_a$, a substituted or unsubstituted $C_1$ to $C_{20}$ alkyl group, a substituted or unsubstituted $C_2$ to $C_{20}$ alkoxy group, a substituted or unsubstituted $C_2$ to $C_{20}$ alkenyl group, a substituted or unsubstituted $C_2$ to $C_{20}$ alkynyl group, a $C_2$ to $C_{20}$ alkylene oxide group, a substituted or unsubstituted $C_3$ to $C_{30}$ cycloalkyl group, a substituted or unsubstituted $C_6$ to $C_{30}$ aryl group, a substituted or unsubstituted $C_6$ to $C_{30}$ aryloxy group, a substituted or unsubstituted $C_6$ to $C_{30}$ heteroaryl group, or a combination thereof, and $R_a$ is hydrogen, a $C_1$ to $C_{10}$ alkyl group, or a $C_6$ to $C_{20}$ aryl group;

$R_4$ is a hydroxyl group, a halogen group, a cyano group, —C(=O)$R_a$, —C(=O)O$R_a$, —OCO(O$R_a$), —C=N($R_a$), —S$R_a$, —S(=O)$R_a$, —S(=O)$_2R_a$, —P$R_a$, a substituted or unsubstituted $C_1$ to $C_{20}$ alkyl group, a substituted or unsubstituted $C_2$ to $C_{20}$ alkoxy group, a substituted or unsubstituted $C_2$ to $C_{20}$ alkenyl group, a substituted or unsubstituted $C_2$ to $C_{20}$ alkynyl group, a $C_2$ to $C_{20}$ alkylene oxide group, a substituted or unsubstituted $C_3$ to $C_{30}$ cycloalkyl group, a substituted or unsubstituted $C_6$ to $C_{30}$ aryl group, a substituted or unsubstituted $C_6$ to $C_{30}$ aryloxy group, a substituted or unsubstituted $C_6$ to $C_{30}$ heteroaryl group, or a combination thereof, and $R_a$ is hydrogen, a $C_1$ to $C_{10}$ alkyl group, or a $C_6$ to $C_{20}$ aryl group; and $R_5$, $R_6$, $R_7$, and $R_8$ are each independently hydrogen, a hydroxyl group, a halogen group, a cyano group, —C(=O)$R_a$, —C(=O)O$R_a$, —OCO(O$R_a$), —C=N($R_a$), —S$R_a$, —S(=O)$R_a$, —S(=O)$_2R_a$, —P$R_a$, a substituted or unsubstituted $C_1$ to $C_{20}$ alkyl group, a substituted or unsubstituted $C_2$ to $C_{20}$ alkoxy group, a substituted or unsubstituted $C_2$ to $C_{20}$ alkenyl group, a substituted or unsubstituted $C_2$ to $C_{20}$ alkynyl group, a $C_2$ to $C_{20}$ alkylene oxide group, a substituted or unsubstituted $C_3$ to $C_{30}$ cycloalkyl group, a substituted or unsubstituted $C_6$ to $C_{30}$ aryl group, a substituted or unsubstituted $C_6$ to $C_{30}$ aryloxy group, a substituted or unsubstituted $C_6$ to $C_{30}$ heteroaryl group, or a combination thereof, where $R_a$ is hydrogen, a $C_1$ to $C_{10}$ alkyl group, or a $C_6$ to $C_{20}$ aryl group; and $R_3$ is a halogen group, a $C_1$ to $C_{20}$ alkyl group substituted with one or more halogen atoms, or a combination thereof; and wherein at least one of $R^5$, $R^6$, $R^7$, and $R^8$ is a hydroxyl group.

10. The inhibitor of claim 9, wherein the KDM is KDM4.

11. The inhibitor of claim 10, wherein the KDM4 demethylates triple methyl groups at lysine NO. 9 of histone subunit NO. 3.

12. A method of inhibiting activity of KDM, wherein the method comprises incubating in vitro the compound of claim 1 and KDM.

13. The method of claim 12, wherein the KDM is KDM4.

14. The method of claim 13, wherein the KDM4 demethylates histone H3 with a tri-methylated lysine in the ninth position.

* * * * *